US012667809B2

(12) United States Patent
Smith et al.

(10) Patent No.: US 12,667,809 B2
(45) Date of Patent: Jun. 30, 2026

(54) AIR PURIFIER WITH AIR TREATMENT BASKET

(71) Applicant: BISSELL Inc., Grand Rapids, MI (US)

(72) Inventors: Derek Smith, Greenville, MI (US);
Habib Baydoun, Dearborn Heights, MI
(US); Morgan Tolles, Hastings, MI
(US); Tyler Grab, Grand Rapids, MI
(US)

(73) Assignee: BISSELL Inc., Grand Rapids, MI (US)

( * ) Notice: Subject to any disclaimer, the term of this
patent is extended or adjusted under 35
U.S.C. 154(b) by 469 days.

(21) Appl. No.: 18/228,144

(22) Filed: Jul. 31, 2023

(65) Prior Publication Data

US 2024/0042384 A1     Feb. 8, 2024

Related U.S. Application Data

(60) Provisional application No. 63/394,412, filed on Aug.
2, 2022.

(51) Int. Cl.
| | |
|---|---|
| *B01D 53/88* | (2006.01) |
| *A61L 9/014* | (2006.01) |
| *A61L 9/20* | (2006.01) |
| *B01D 46/00* | (2022.01) |
| *B01D 53/00* | (2006.01) |
| *B01D 53/86* | (2006.01) |

(52) U.S. Cl.
CPC ............ *B01D 53/885* (2013.01); *A61L 9/014*
(2013.01); *A61L 9/205* (2013.01); *B01D
46/0028* (2013.01); *B01D 53/007* (2013.01);
*B01D 53/8634* (2013.01); *A61L 2209/12*
(2013.01); *A61L 2209/14* (2013.01); *A61L*

*2209/22* (2013.01); *B01D 2253/102* (2013.01);
*B01D 2255/50* (2013.01); *B01D 2255/802*
(2013.01); *B01D 2257/406* (2013.01); *B01D
2257/708* (2013.01); *B01D 2257/91* (2013.01);
*B01D 2259/804* (2013.01)

(58) Field of Classification Search
CPC ..... A61L 9/014; A61L 9/205; B01D 46/0028;
B01D 46/0005; B01D 46/10; B01D
46/2403; B01D 46/2422; B01D 46/60;
B01D 53/885; B01D 53/007
See application file for complete search history.

(56) References Cited

U.S. PATENT DOCUMENTS

| | | | | |
|---|---|---|---|---|
| 2008/0295271 A1* | 12/2008 | Perunicic | ............... | A47L 11/405 |
| | | | | 15/246.3 |
| 2018/0221805 A1* | 8/2018 | Bae | ......................... | B01D 46/44 |
| 2023/0073240 A1* | 3/2023 | Yang | .................... | B01D 53/007 |
| 2023/0135626 A1* | 5/2023 | Bang | .................... | B01D 53/885 |
| | | | | 422/121 |

OTHER PUBLICATIONS

U.S. Appl. No. 18/228,120 entitled Air Purifier with Rotatable Filter
filed Jul. 31, 2023.

* cited by examiner

*Primary Examiner* — Donald R Spamer
*Assistant Examiner* — Kayla Rose Sarantakos
(74) *Attorney, Agent, or Firm* — Warner Norcross + Judd
LLP

(57)     ABSTRACT

An air purifier and air treatment basket for inside air. The air
purifier includes a housing. The air treatment basket is
disposed in the housing. The air treatment basket includes an
air treatment basket frame and a plurality of selectively
removable air treatment panels containing filter media.

20 Claims, 9 Drawing Sheets

AIR PURIFIER WITH AIR TREATMENT BASKET

BACKGROUND

The present disclosure relates to air purifiers. In particular, the present disclosure relates to a filter media basket that aids uniform air distribution with the filter media without significantly reducing air flow through the unit.

Many floor stand air purifiers have air inlets along the outside perimeter toward the bottom of the unit with a central fan that draws air horizontally through the inlets, through a filter, and then vertically through the air treatment chamber, expelling treated air toward the top of the unit. To provide high airflow surface area through the filter media, often a cylindrical high efficiency particulate air (HEPA) filter is installed within the airflow chamber such that the perimeter of the filter lies near the air inlets. While the cylindrical filter can provide effective air purification in many situations, there are some applications where additional filter media within the air treatment chamber is desired. However, adding additional filter media to the air treatment chamber presents a variety of different challenges. Some of the potential issues with adding additional filter media to an air treatment chamber can include hampering airflow, which can have a negative impact on air treatment, and difficulty in providing easy replacement access for the additional filter media.

BRIEF DESCRIPTION

An air purifier having an air treatment basket with filter media to capture, absorb, and/or remove odor causing volatile organic compounds (VOCs) from inside air is provided herein. Aspects of the disclosure relate to an air purifier including a housing, an air flow path, a blower, and an air treatment basket. The various features of the air treatment basket promote uniform airflow through the air treatment basket filter media while reducing airflow restriction.

The housing includes an air inlet, air treatment chamber, and an air outlet fluidly connected by the air flow path. The blower may be disposed within the housing and is configured to draw air into the housing through the air inlet along the airflow path, and push air out of the housing through the air outlet. The air treatment basket can be configured to at least one of filter, clean, and purify air flowing through the air flow path. The shape and position of the filter basket can facilitate uniform and unrestricted airflow through the air treatment chamber of the housing.

The air treatment basket can include multiple air treatment panels that removably couple to the air treatment basket to facilitate easy removal while the air treatment basket is installed within the air treatment chamber of the air purifier.

Aspects of the disclosure relate to an air treatment panel for use in an air treatment basket. The air treatment panels can each have a filter matrix of cells containing filter media granules, pellets, or particulate filter media retained in the cells by a retaining mesh. The panel can include a coupler configured to removably couple the panel to the air treatment basket.

The air treatment basket can be conically shaped and surround a UV light source to facilitate a photocatalytic oxidation (PCO) reaction with the filter media in the air treatment basket. By tilting the panels of the air treatment basket inward toward the center of the air treatment chamber and away from the air inlet, airflow through the base of the basket is reduced and there is more surface area for airflow through the side panels. That is, by tilting the faceted panels inward, the airflow tends to reach more of the surface area of each panel in a more even way, which leads to more even and consistent air treatment.

These and other features and advantages of the present disclosure will become apparent from the following description of particular embodiments, when viewed in accordance with the accompanying drawings and appended claims.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. In addition, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

DETAILED DESCRIPTION

Figure 1:
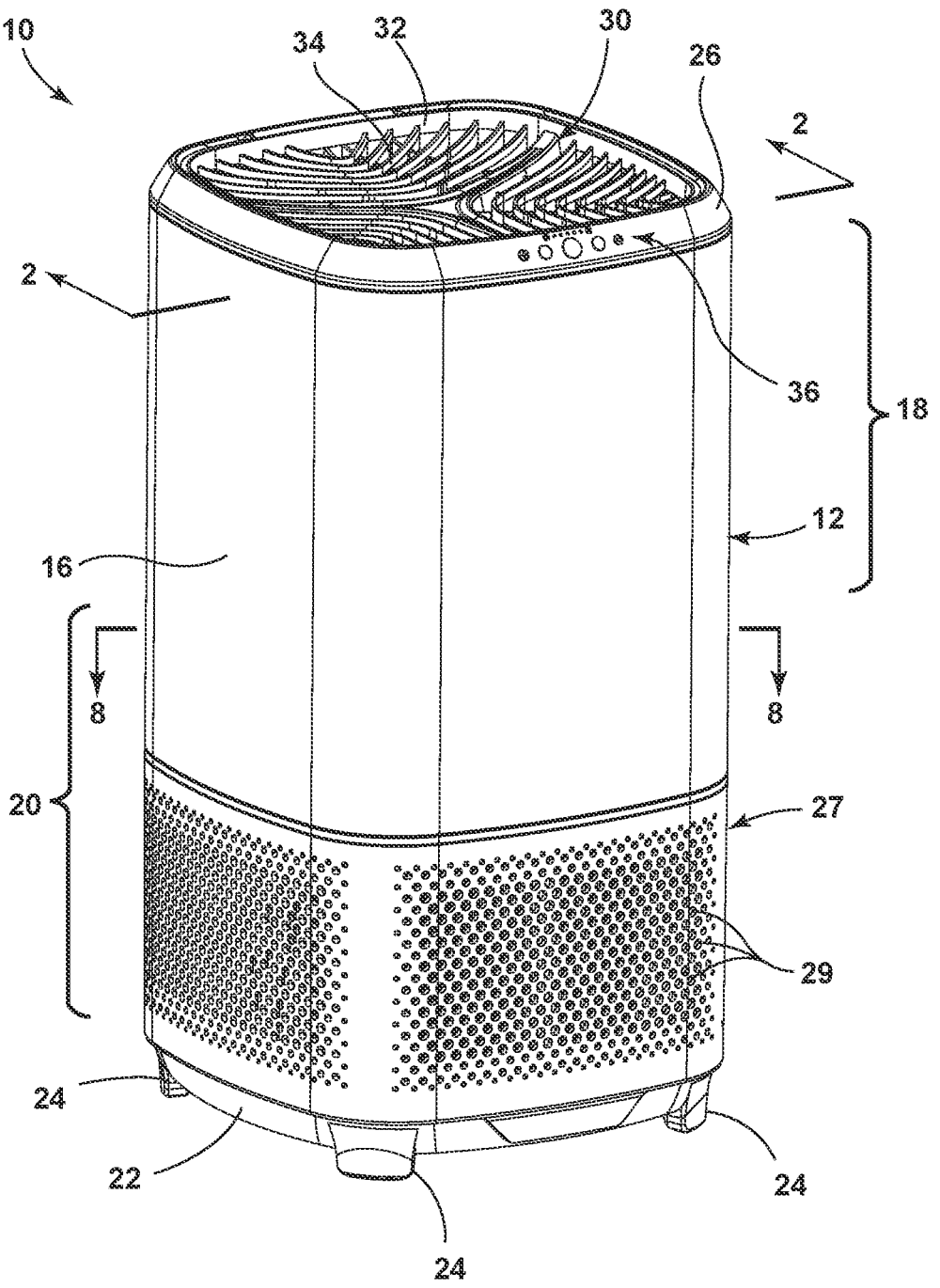
FIG. 1 is a perspective view of an air purifier with an air treatment basket according to various aspects described herein.

Aspects of the disclosure relate to an air purifier with an air treatment basket and/or an air treatment basket for use in conjunction with an air purifier. While primarily discussed herein in terms of an air purifier for indoor air, aspects of the air treatment basket and embodiments thereof disclosed herein are applicable to other types of air filtration devices.

The term "clean" as used herein is to describe the removal of pollutants from air as compared to the ambient air. Pollutants can include dirt, dust, volatile organic compounds (VOCs), biological contaminants (e.g., bacteria, viruses, mold spores, waste products, etc.), soot particles, and any other pollutants that can be found in indoor and/or outdoor flows.

The term "purify" is used herein to describe killing or inactivating biological contaminants, pathogens, or microorganisms in the ambient air. It is noted that the air purifier apparatus can have a variety of applications including commercial or home based applications.

As used herein, the term "upstream" refers to a direction that is opposite the air flow direction, and the term "downstream" refers to a direction that is in the same direction as the air flow. Additionally, as used herein, the terms "radial" or "radially" refer to a direction away from a common center. Furthermore, as used herein, the term "set" or a "set" of elements can be any number of elements, including only one.

All directional references (e.g., radial, axial, proximal, distal, upper, lower, upward, downward, left, right, lateral, front, back, top, bottom, above, below, vertical, horizontal, clockwise, counterclockwise, upstream, downstream, etc.) are only used for identification purposes to aid the reader's understanding of the present disclosure, and do not create limitations, particularly as to the position, orientation, or use of aspects of the disclosure described herein. Connection references (e.g., attached, coupled, secured, fastened, connected, and joined) are to be construed broadly and can include intermediate members between a collection of elements and relative movement between elements unless otherwise indicated. As such, connection references do not necessarily infer that two elements are directly connected and in fixed relation to one another. The exemplary drawings are for purposes of illustration only and the dimensions, positions, order, and relative sizes reflected in the drawings attached hereto can vary.

Figure 2:
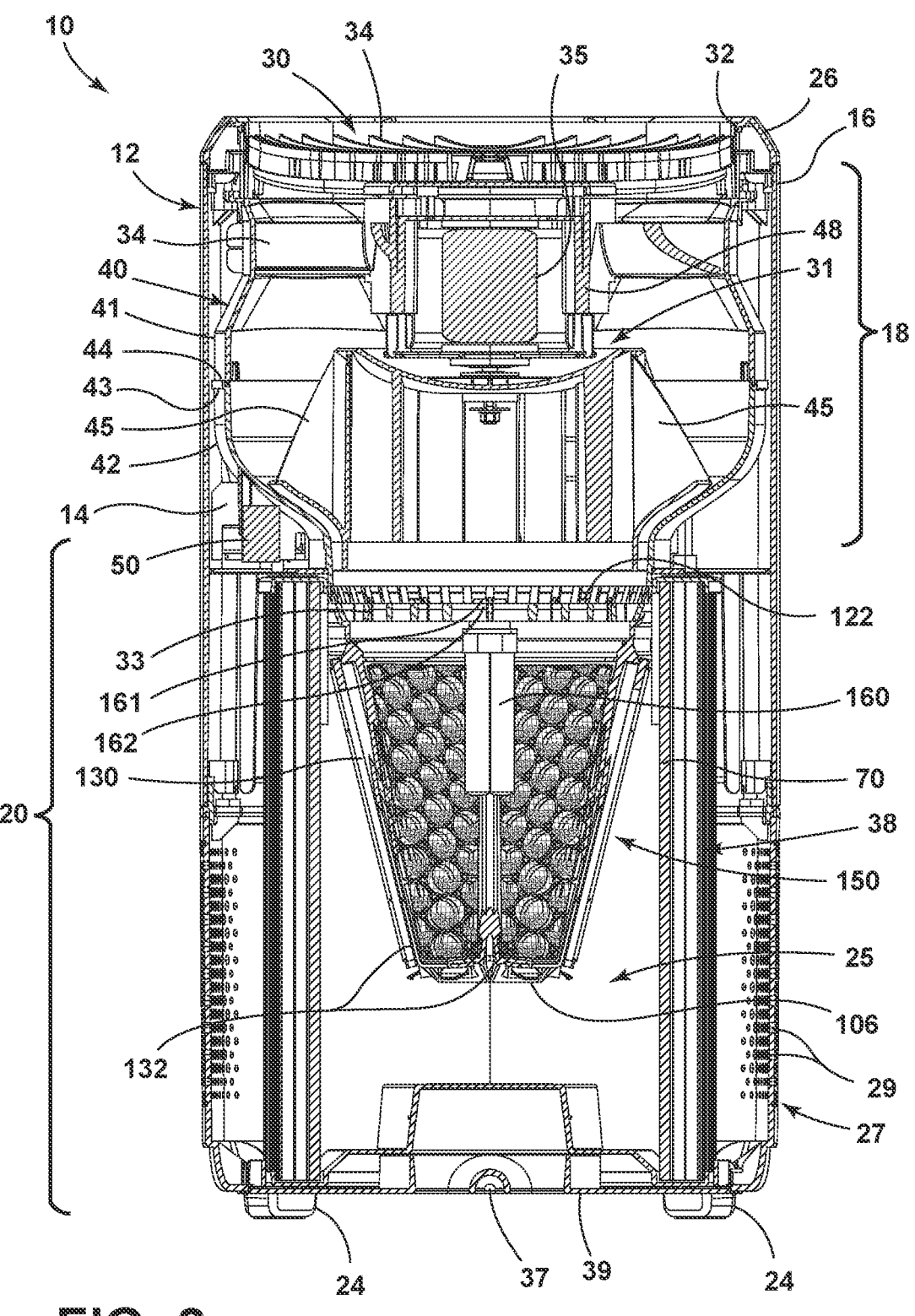
FIG. 2 is a sectional view of the air purifier with an air treatment basket of FIG. 1 along the line 2-2.
Figure 3:
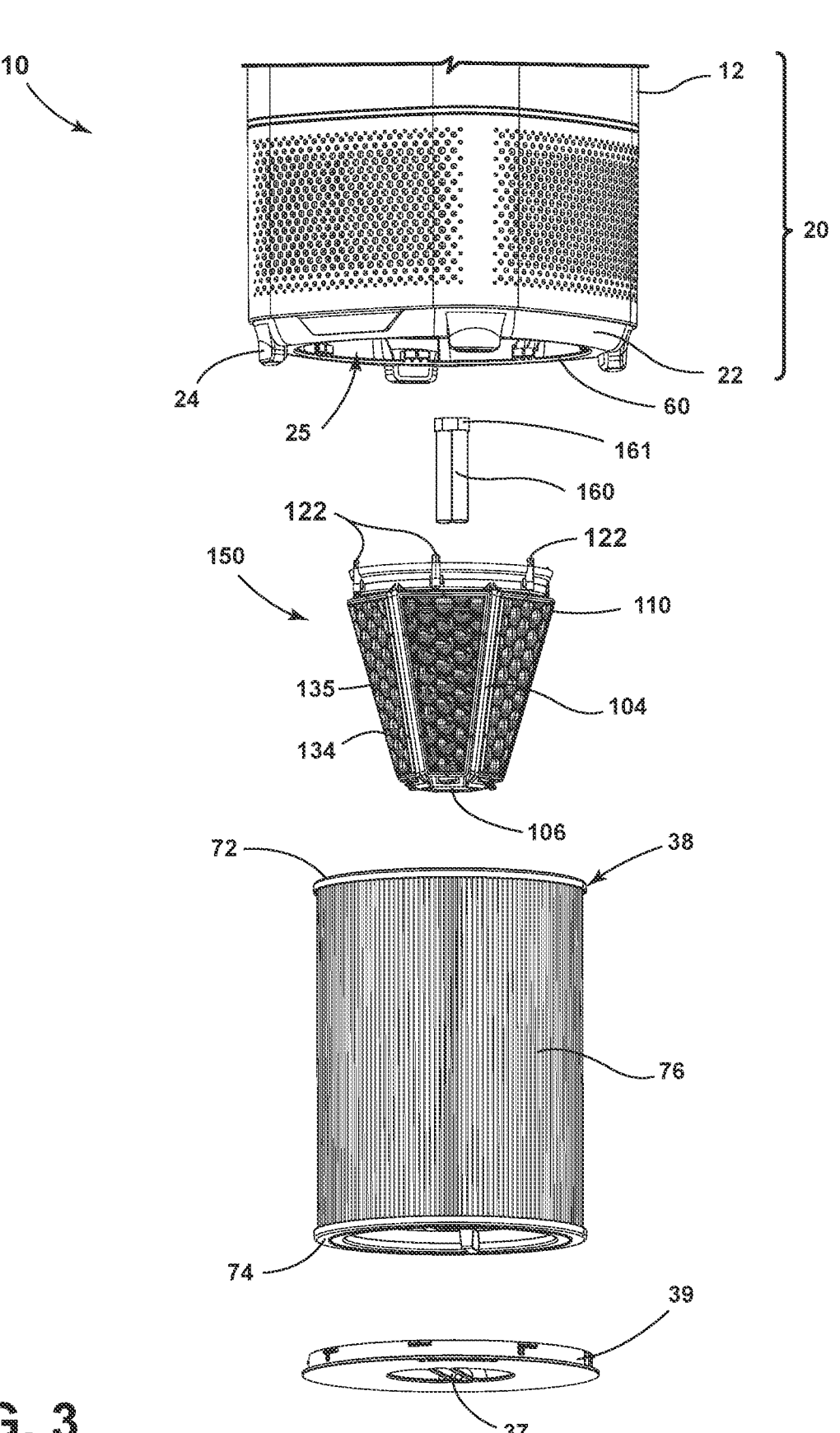
FIG. 3 is a partial exploded view of the air purifier, germicidal light source, air treatment basket, and cylindrical filter of FIG. 1.

FIGS. 1-3 illustrate an exemplary air purifier 10 in conjunction with one embodiment of the present disclosure. Referring to FIG. 1, a perspective view of the air purifier is shown illustrating the general structure of the air purifier housing 12 along with externally viewable features and components.

The air purifier housing 12 can be a monolithic body, e.g., a single body that is a single, non-separable piece, or formed as a single unitary piece at manufacture, as opposed to being formed by combining separate elements into one during manufacture. Alternatively, the housing 12 can be defined by more than one component coupled together. The shape of the housing 12, as illustrated by way of example is a prism having a base or cross-sectional shape that is a squircle (e.g., a shape intermediate between a square and a circle), however it is contemplated that the housing 12 can be any shape, such as, but not limited to, a cylinder having a base or cross-sectional shape that is a circle, a round rectangular prism having a base or cross-sectional shape that is a rounded rectangle or a square, or an elliptic cylinder having a cross-sectional shape that is an ellipse or oval. The air purifier housing 12 can be manufactured from a variety of suitable materials, such as common plastic housing materials including, Acrylonitrile Butadiene Styrene (ABS), High Density Poly Ethylene (HDPE), polycarbonate, and polypropylene, to name a few suitable options. A decorative covering 16 may surround a portion of the housing 12.

To aid with description of the air purifier's components and features, the housing 12 is labeled with an upper portion 18 and a lower portion 20. Although the illustrated labels divide the housing roughly in half, it is contemplated that the upper portion 18 can be larger or smaller, with the lower portion 20 defining the remaining portion of the housing 12.

Cover trim 26 can surround the outside upper edge of the housing 12 to provide a clean aesthetic edge and surface for an air purifier user interface 36. In the current embodiment, the cover trim 26 is joined to the upper portion 18 of the housing 12 and the upper fan shroud top edge 32.

An air purifier user interface 36, to the extent one is provided directly on the air purifier, can be mounted to or formed with the housing 12 or provided elsewhere on the air purifier. In the current embodiment, the user interface 36 for controlling operation of the air purifier is integrated into the external surface of the cover trim 26.

The user interface 36 can include various features and user interface elements including, but not limited to, indicator lights providing information about the air purifier 10 to the user and/or buttons that adjust one or more settings or change the status of one or more components of the air purifier 10. While a single user interface 36 is shown, it is contemplated that the air purifier 10 can include more than one user interface. Optionally, the air purifier 10 can be remotely controlled by one or more electronic devices such as, but not limited to, a handheld remote or a mobile phone. The user interface 36 can include or be electrically coupled to a control system 50 (See FIG. 2) located elsewhere in the air purifier.

The air outlet 30 can be provided in various locations and configurations on the housing 12. For example, the air outlet 30 can be provided toward the top end of the air purifier housing 12. In the current embodiment, the air outlet 30 is disposed within the internal perimeter of the cover trim 26 of the housing 12, and may be referred to as a vent. The vent can include a plurality of flow diverters 34, which define a plurality of openings therebetween. While illustrated generally as radially extending vanes, the flow diverters 34 can be uniform or dynamic in essentially any shape, size, number, profile, spacing, layering, and orientation to provide a desired venting profile and aesthetic appearance. The flow diverters 34 can be single piece components or assemblies defined by two or more flow diversion components.

The lower portion 20 of the housing 12 generally includes an air inlet 27 and a base 22. The base 22 can include legs 24 or other supports. In the depicted embodiment, four legs 24 are disposed at the outer bottom corners of the base 22 to support the air purifier in an upright standing position.

The air inlet 27 can be provided in various locations and configurations on the housing 12. By way of example, the air inlet 27 can include a plurality of perforations 29 in the lower portion 20 of the housing 12. The plurality of perforations 29 can be included on one or any number of sides of the housing 12. In the current embodiment all four sides of the housing 12 have a set of perforations 29 that each permit air to enter into the air treatment chamber 25 (see FIG. 2). The plurality of perforations 29 can be generally uniform or dynamic in size, number, and shape. In the depicted embodiment, the perforations 29 are organized into generally rectangular patterns on each side of the bottom portion 20 of the housing 12. Near the perimeter of the rectangular patterns on each housing face, the diameter of the perforations are smaller while near the center of the rectangular patterns the diameters of the perforations are larger.

Referring to FIG. 2, a sectional view of the air purifier 10 along the line 2-2 is shown illustrating internal components of the air purifier housing 12 as well as internal support structure of the housing 12, air inlet 27, and air outlet 30. In the depicted embodiment, the internal components of the air purifier generally include a control system 50, blower 31, and fan shroud 40 disposed in the upper portion 18 of the housing along with an inlet air treatment device 38, a germicidal light source 160, and an air treatment basket 150 disposed within an air treatment chamber 25 in the lower portion of the air purifier housing 12.

The control system 50 can be electrically coupled to the blower 31 as well as the user interface 36. The control system 50 can be configured to control operation of the fan motor 35 according to user input via the user interface 36. For example, the control system 50 can be configured to receive and respond to fan speed adjustment signals by communicating fan speed signals to the fan motor to adjust fan speed. In one embodiment, there are five fan speed settings ranging from low to high. The fan speed may also include an automatic mode setting where the fan speed is dynamically and automatically controlled by the control system 50 according to indoor air quality readings, other sensor readings, or a predetermined fan speed profile. For example, one or more sensors, such as a light sensor and/or volatile organic compounds (VOC) sensor can be included in the air purifier. The one or more sensors can be disposed in essentially any suitable location in the housing and in electrical communication with the control system 50.

Although the control system 50 is disposed within the interior 14 of the upper portion 18 of the housing 12 adjacent the fan shroud 40, in alternative embodiments, the control system 50 can be disposed elsewhere within the air purifier 10 or distributed at multiple locations within the interior 14 of the air purifier. The control system 50 or portions thereof can include a printed circuit board ("PCB"), microcontroller, and one or more other electronic components. The control system 50 may be electrically powered by an electrical connection to a power outlet via electrical cord 80 (See FIG. 8). Alternatively, the control system 50 can be powered by a battery or other power supply circuitry.

The blower 31 can include a set of fan blades 45 coupled to a fan motor 35 to drive the fan blades 45 in order to generate airflow, which is channeled toward the air outlet 30 by the fan shroud 40. In general, while the fan motor 35 is energized, air is drawn through the air inlet 27, the air treatment chamber 25, the fan shroud 40, and pushed out of the air outlet 30.

The illustrated embodiment of the fan shroud 40 has a two-piece construction with a lower fan shroud 42 and an upper fan shroud 41. The top end of the lower fan shroud 42 includes a channel 43 that receives the lower edge 44 of the upper fan shroud 41 to form the complete fan shroud 40. In alternative embodiments the fan shroud 40 can have a monolithic construction, e.g., a single body that is a single, non-separable piece, or formed as a single unitary piece at manufacture, as opposed to being formed by combining separate elements into one during manufacture. The shape of the fan shroud 41, as illustrated by way of example is generally vase-shaped where the bottom surface of the airflow grill 33 of the lower shroud 42 is generally flat, the shroud body curves outward to facilitate airflow around the motor housing 48, then back inward to facilitate airflow through openings between flow diverters 34 of the upper fan shroud 41 and out the air outlet 30. In alternative embodiments, the fan shroud 40 can have a different shape that suitably facilitates airflow from the air treatment chamber 25 to the air outlet 30.

In the current embodiment, the blower 31 is disposed in the upper portion 18 of the housing 12, while the inlet air treatment device 38 and the air treatment basket 150 are disposed in the lower portion 20 of the housing 12, generally below the blower 31. The blower 31 and the air treatment basket 150 are separated by the airflow grill 33 of the lower fan shroud 42. That is, in the current embodiment, the airflow grill 33 of the lower fan shroud 42 generally separates the inlet air treatment device 38 and air treatment basket 150 in the air treatment chamber 25 in the bottom portion 20 of the housing 12 from the fan shroud 40 and blower 31 in the upper portion 18 of the housing 12. In the current embodiment, the inlet air treatment device 38 and the air treatment basket 150 are disposed within the airflow path upstream of the blower 31 such that air is drawn from the air inlet 27 through the air treatment components. However, other spatial arrangements are possible, for example where the blower 31 pushes air through the air treatment components, or a combination of pushing air through one or more air treatment components and drawing air through one or more other air treatment components.

Figure 4:
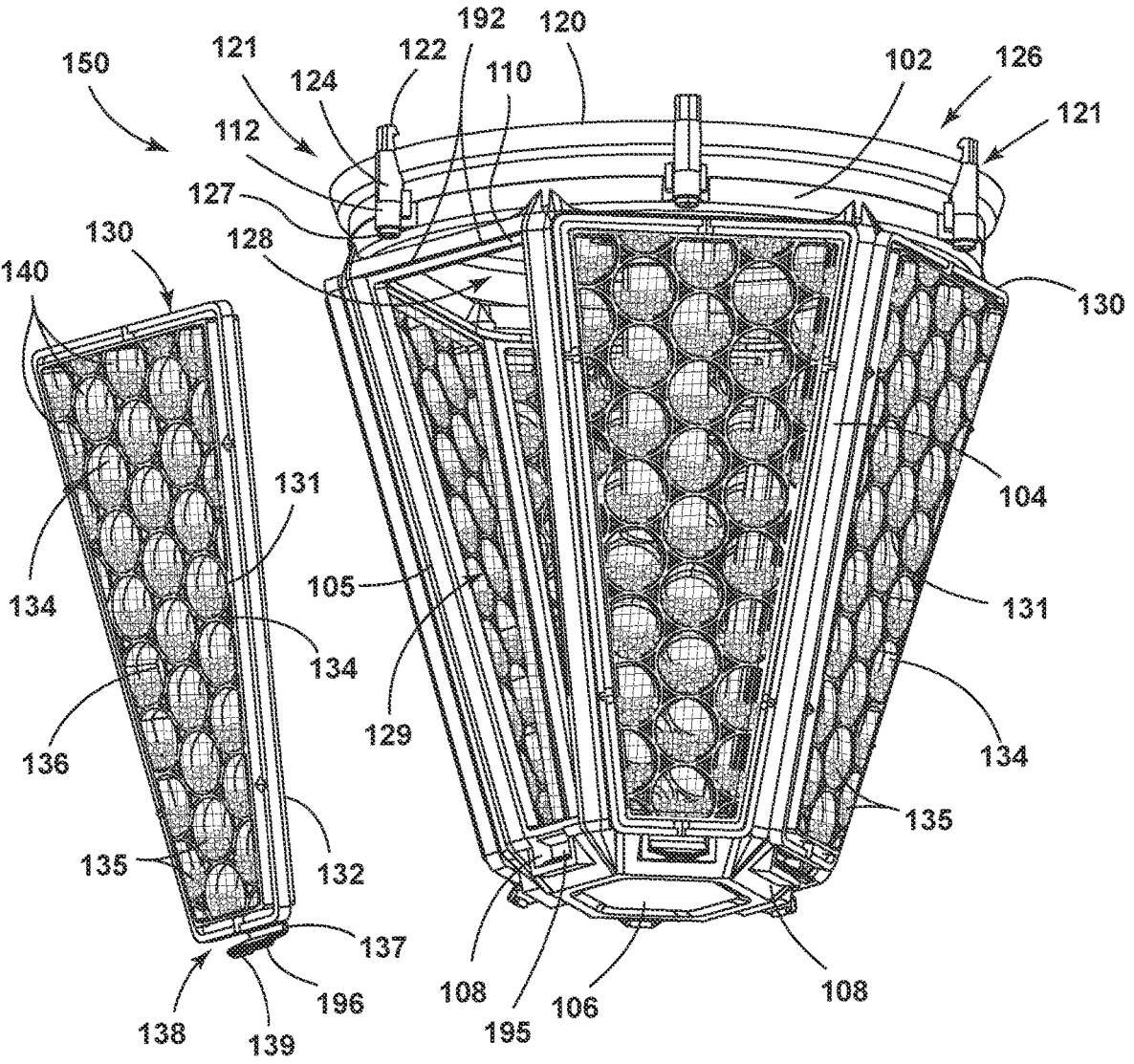
FIG. 4 is a perspective view of an air treatment basket with a portion exploded according to one embodiment.

The air treatment basket 150 can mount to the airflow grill 33 of the lower fan shroud 42 with one or more coupling assemblies 122 (perhaps best shown in FIG. 4). The air treatment basket 150 can be configured to span the airflow grill 33 such that a majority of air flowing through the air treatment chamber 25 generally passes through one of the air treatment panels 130 installed in the air treatment basket frame 104 of the air treatment basket 150 to reach the air outlet 30. In its installed state, the air treatment basket 150 can surround the germicidal light source 160. In some alternative embodiments, the air treatment basket 150 can be joined or integrally formed with the housing 12, another part of the lower fan shroud 42, or another air purifier component. In other alternate embodiments, the basket 150 can be removably mounted to the airflow grill 33. Various details regarding the air treatment basket 150, its attachment to the airflow grill 33, and its functionality will be discussed in more detail below in connection with FIG. 4.

Figure 8:
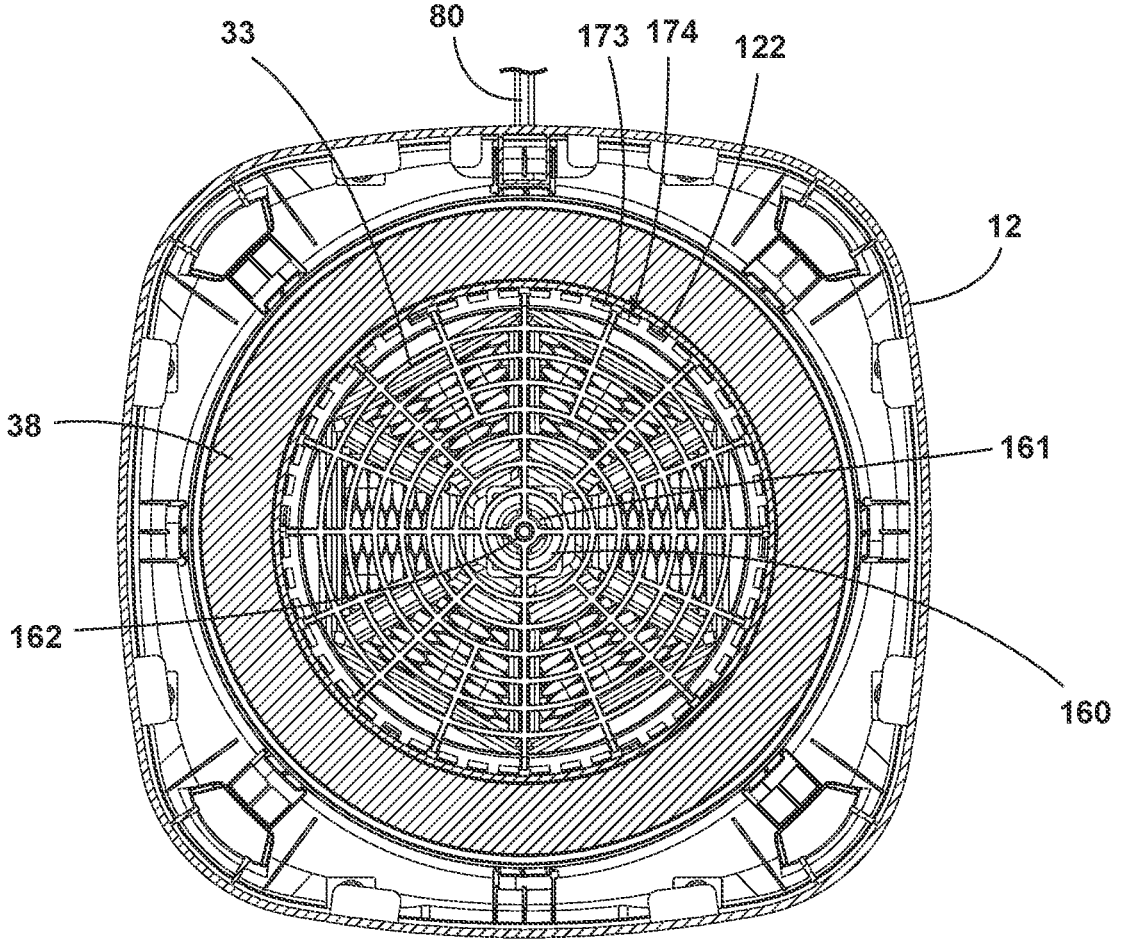
FIG. 8 is a sectional top down view of the air purifier of FIG. 1 along the line 8-8.

A germicidal light source 160 can be included in the air purifier to assist with air treatment. In one embodiment, the germicidal light source 160 is an ultraviolet (UV) light bulb, specifically a UV-C bulb that can aid with air treatment. The germicidal light source 160 is disposed within the air treatment chamber 25. Referring to FIG. 2, in the illustrated embodiment, the germicidal light source 160 is coupled to the airflow grill 33 such that it hangs down into the center of the air treatment chamber 25 about equidistant from the air treatment panels 130 of the air treatment basket 150. Perhaps as best shown in FIG. 8, the germicidal light source 160 can be joined to the center ring 162 of the airflow grill 33 by four germicidal light fasteners 161 that snap around the center ring 162 of the airflow grill 33. In alternative embodiments, the germicidal light source 160 can be mounted elsewhere within the air treatment chamber or mount to other structure or components of the air purifier 10. The germicidal light source 160 can be removably mounted in the air purifier 10 such that it can be easily removed from the housing and replaced as needed. Some embodiments may not include a germicidal light source 160 at all. FIG. 8 does not include the filter material 135 for visual clarity of the depicted components.

Returning to FIGS. 2-3, the inlet air treatment device 38 can include a cylindrical filter support 70, two filter support ends 72, 74, and air treatment media 76. The air treatment media 76 can have an accordion shape that wraps around the cylindrical filter support 70 and is held in place by the two filter support ends 72, 74. The inlet air treatment device 38 can be removably installable within the air treatment chamber 25 positioned adjacent the internal side of the air inlet 27. The air treatment media 76 can include essentially any suitable air treatment media or combination of air treatment media, including for example, a filter, an ion injector, or any combination thereof, and including multiples thereof. The air treatment media 76 of the inlet air treatment device 38 can be tailored to cooperate with the air treatment media of the air treatment basket 150 such that the air treatment device 10 as a whole provides satisfactory and suitable air treatment quality and efficiency. In the current embodiment, the air treatment media 76 can be a 3-in-1 filter including a pre-filter and combination of carbon and a high efficiency particulate air HEPA filter. The pre-filter can be configured to capture large dust particles and hair, the carbon filter can be configured to absorb odors and VOCs, and the HEPA filter can be configured to capture pollen, pet dander, smoke, and fine dust particles. In other embodiments, instead of a 3-in-1 or other type of air treatment media, the inlet air treatment device 38 may include HEPA filter without a pre-filter or carbon filter.

FIG. 3 illustrates a partial exploded view of a bottom portion 20 of the housing 12 of the air purifier 10. The germicidal light source 160, air treatment basket 150, inlet air treatment device 38, and cover 39 are shown exploded away from their installed positions within the air treatment chamber 25.

The inlet air treatment device 38 can be selectively removable from the air purifier 10, for example by turning the air purifier 10 upside down, grabbing a removal handle 37, and twisting the removable cover 39 from a locked position to an unlocked position, and removing the bottom cover 39 to provide access through the bottom opening 60 of the base 22 to the air treatment chamber 25. The inlet air treatment device 38 can then be lifted out of the air purifier 10. In the current embodiment, the air treatment device 38 and the cover 39 are separate components, but in alternative embodiments the air treatment device 38 and cover 39 can be joined together or integrally formed such that twisting and removing the cover 39 also removes the air treatment device 38. The air treatment device 38 and cover 39 can be removably coupleable. In one embodiment, the cover 39 can be removed from a used inlet air treatment device 38 and re-coupled to a ready-to-use air treatment device.

FIG. 4 illustrates the air treatment basket 150 with a portion removed according to an aspect of the present disclosure. The basket 150 includes a top attachment assembly 126 and a base 106 spaced apart from the top attachment assembly 126 by an air treatment basket frame 104. The air treatment basket frame 104 defines a plurality of air treatment panel seats 129 that each receive a separate air treatment panel 130. The top attachment assembly 126 and a top portion of the air treatment basket frame 104 cooperatively and generally define a treated air exit aperture 128. The base 106 can be solid as shown by example in FIG. 4, or alternatively can define an inlet aperture. The top attachment assembly 126, base 106, and air treatment basket frame 104 define an interior of the basket 150.

The basket frame 104 can have a monolithic, i.e., one-piece, construction, or be manufactured in two or more separate pieces and assembled by a suitable joining method such as adhesion, gluing, bonding, welding, or the like. In the depicted embodiment, the basket frame 104 is a single component construction.

The basket frame 104 can be manufactured from one or more different types of materials. For example, the basket frame 104 and supplementary basket components (e.g., coupling ring 120 and base 106) can be constructed from a common plastic housing material such as Acrylonitrile Butadiene Styrene (ABS), High Density Poly Ethylene (HDPE), polycarbonate, and polypropylene, to name a few suitable options. Suffice it to say, the basket frame may be manufactured from a material that generally does not permit airflow, such that airflow toward the basket 150 is forced through the air treatment panels 130.

In the current embodiment, the top attachment assembly 126 includes a top rim 102 of the basket frame 140, a coupling ring 120, and one or more coupling assemblies 121. In alternative constructions, the top attachment assembly 126 can have additional, different, or fewer components. In the depicted embodiment, the coupling assemblies 121 serve a dual purpose of both attaching the frame 104 to the coupling ring 120 (via screws 127) and also attaching the coupling ring 120 to the airflow grill 33 (via cantilevers 122 snap fitting to the airflow grill 33). In alternative constructions, the coupling ring 120 may be omitted, and the coupling assemblies can directly mount the basket frame 104 to the airflow grill 33 or other air purifier components.

Each coupling assembly 121 generally includes a frame protrusion 112, a ring protrusion 124, a screw 127, and a snap fit cantilever 122. The frame protrusion 112 extends outward from the outer surface of the top rim 102 of the air treatment basket frame 104. The ring protrusion 124 extends outward from the outer surface of the coupling ring 120. The frame protrusion 112 is formed complementarily to the ring protrusion 124 such that the coupling ring 120 is coupleable to the top rim 102 of the basket frame 104 by the complementary connection of the frame protrusion 112 and the coupling protrusion 124. In the current embodiment, the ring protrusion 124 and coupling ring 120 include aligned apertures suitable for a screw 127 to fixedly secure the top rim 102 to the coupling ring 120. Operation of the coupling assemblies will be described below in more detail in connection with FIG. 5.

The size and shape of the treated air exit aperture 128 of the top attachment assembly can vary depending on a variety of different factors, such as the overall size of the air purifier, the size and shape of the air treatment basket 150, desired airflow rate, and shape/size/pattern of the airflow grill 33, to name a few. The circumference of the treated air exit aperture 128 can be smaller, larger, or the same as the base 106.

As depicted in FIG. 4, the base 106 of the air treatment basket 150 can be a solid material that does not permit airflow into the air treatment basket 150. A solid base 106 prevents airflow and generally diverts airflow elsewhere in the air treatment chamber, such as to the air treatment basket 150 through the plurality of air treatment panels 130. The base 106 may be integrally formed with the basket frame 104 or joined with the basket frame 104. In another embodiment, the base 106 can be removably coupled to the basket frame 104.

In the depicted embodiment, the basket frame 104 generally has six air treatment panel seats 129. Each air treatment panel seat 129 generally includes a perimeter surface 191 of the basket frame 104 that defines an air treatment panel receiving aperture 105 as well as a panel support ledge 110 that extends from the perimeter surface 191 further defining the air treatment panel receiving aperture 105. Each perimeter surface 191, panel support ledge 110, and air treatment panel receiving aperture 105 cooperatively form an air treatment panel seat 129 configured to receive and align one of the air treatment panels 130. Alternative constructions can include additional or fewer air treatment panel seats 129 and panels 130.

The basket frame 104 can include one or more retaining elements that cooperate with the air treatment panels 130 to retain the air treatment panels 130 within the air treatment panel seats 129. In the depicted embodiment, the perimeter surface 191 of the basket frame 150 includes two retaining slots 192 along the top edge of the perimeter surface 191 along with a channel 108 and catch 195 that forms a snap fit air panel interlock with the air treatment panel. Operation of the interlock will be further described below in connection with FIG. 9.

Each air treatment panel 130 includes a panel frame 132 holding a filter media 135. The air treatment panel 130 may alternately be referred to as a facet of the air treatment basket 150. The panel frame 132 surrounds a filter media matrix 131 defining a plurality of cells 140. The panel frame 132 may be a plastic component manufactured via injection molding, e.g. with the matrix 131 and cells 140 integrally formed by the molding process. The air treatment panels 130 may be constructed from recyclable, biodegradable and/or compostable material, or combinations thereof. After injection molding, a filter media 135 can be added to the matrix 131, for example by filling at least some, alternatively all, cells 140 with a granulate, particulate, or pelletized filter media 135. The filter media 135 can be disposed in at least some, alternatively all, of the cells 140. A retaining mesh 136 can be disposed on the outer and inner sides of the matrix 131 to contain the filter media 135 within the matrix 131. In some embodiments, the matrix 131 can be omitted and instead of granulated, particular, or pelletized filter media, a filter media sheet or block can be housed within the panel frame 132.

The matrix 131 can have a variety of different cell patterns depending on the application. For example, the cells 140 of the matrix can be generally uniform or dynamically sized and the cells 140 can be generally uniformly spaced across the matrix 131 or arranged in a dynamic pattern to facilitate a desired airflow pattern through the matrix. As depicted, the cells 140 are circular structures of generally equal size spaced uniformly to fill the air treatment panel frame 132. In one embodiment, the cells 140 may be hexagonal and arranged in a honeycomb configuration. In some embodiments, the cells 140 can be oriented on an angle relative to the panel frame 132. Some orientations can simplify manufacturing in the case of an injection-molded frame 132.

As depicted, each cell 140 is partially filled with the filter media 135. In one embodiment, the filter media 135 may fill roughly fifty percent of each cell 140. In another embodiment, the filter media 135 can fill essentially any other suitable percentage of the cell 140 up to and including 100% of the cell. In some embodiments, at least some of the cells 140 can be purposely underfilled or left empty, e.g., can lack filter media 135, which can facilitate bypass airflow through the matrix 131 and limit air flow restriction. In some embodiments, open space may be inserted between the matrix cells 140 to facilitate bypass airflow as well.

The filter media 135 is contained by the air treatment panel 130. The filter media 135 is configured to capture, absorb, and/or remove odor causing VOCs. In certain embodiments, the filter media 135 is chosen from carbon, zeolite (understood to include at least zeolite X, zeolite Y, ultrastable zeolite Y, ZSM zeolite, offretite, and beta zeolite, among others), silica gel, faujasite, chabazite, clinoptilolite, mordenite, silicalite, metal organic frameworks, metal oxide, polymers, resins, and combinations thereof. In one embodiment, the filter media 135 is activated carbon pellets mixed with zeolites specific to ammonia removal.

When the air treatment panel 130 is installed within the basket frame 104, gravity causes the filter media 135 to collect toward the bottom of each cell 140 creating an open space 134 above the filter media 135 in each cell 140. The distribution of the filter media 135 within the cell 140 depends not only on the filter media fill percentage of the cell, i.e., how much filter media is in a particular cell, but also the panel angle when seated in the filter media basket 150, the relative orientation of the cell 140 to the panel 132, and the specific matrix 131 parameters (e.g., cell size, cell shape, and cell pattern).

In general, air flows into the air treatment basket 150 through the filter matrix 131 of the air treatment panels 130 and exits the air treatment basket 150 through the exit aperture 128. During operation, the blower 131 draws air through the filter media 135 in each cell 140 to capture, absorb, and/or remove odor causing VOCs. In addition, some air flows unrestricted through the open space 134 in each cell 140 adjacent to the filter media 135.

The distribution of the filter media 135 in the air treatment panels 130 can affect the efficiency and effectiveness of the air treatment provided by the panel 130 and the airflow throughout the air purifier 10. The various parameters of the air treatment panel 130 can be selected to provide a desired filter media distribution throughout the cells 140 of the matrix 131. The orientation of the cells 140 relative to the panel and air treatment basket frame 150 can cooperate with the fill percentage to provide a suitable filter media distribution and desired airflow profile through the filter media matrix 131, which can provide improved air treatment and airflow through the filter media matrix 131 generally.

By virtue of the cell structure and only partially filling the cells 140 with filter media, multiple airflow paths through the filter media matrix 131 are permitted with a tailored airflow pattern that depends on the filter media distribution within the cell. In general, the open space 134 in each cell allows air to bypass the filter media 135 so as to not suffocate the air purifier 10 airflow. For example, by filling each cell with roughly the same amount of filter media (e.g., 50%), the airflow through the panel can be generally uniform because the unrestricted airflow paths are distributed across the filter media matrix. The airflow profile through the filter media matrix 131 can be selectively tailored by changing the filter media distribution (e.g., by changing the filter media fill percentage for the cells 140 or other air treatment panel 130 parameters). For example, by filling the cells 140 toward the bottom of the matrix with a higher percentage of filter media, the airflow profile through the panel can be changed such that airflow is higher in the cells 141 with lower fill percentage by virtue of there being more open space for the air to pass through. Accordingly, by dynamically changing the filter media distribution within the cells, the airflow profile for a panel can be dynamically tailored to provide suitable air treatment with a suitable airflow pattern. For example, the airflow profile can be tailored to match an incoming airflow profile of the air inlet.

The air treatment basket 150 can be configured to contain essentially any amount and/or type of filter media 135. For example, the air treatment basket 150 can include essentially any amount and/or type of filter media for a specific odor rich area. For example, the air treatment basket 150 can contain activated carbon pellets used to adsorb VOCs and mixed with Zeolites specific to ammonia removal to more effectively remove cat litter odors from a litter box area. The air treatment basket 150 may include more than one type of filter media 135. Also, a user can customize the filter media 135 inside the basket 150 depending on the specific odor to address. Users benefit from both the effective odor removal and the customizability of the filter media 135 to meet their odor removal requirements.

A retaining mesh 136 extends across both faces of each air treatment panel 130 to retain the filter media 135 within the cells 140 without significantly reducing airflow. The retaining mesh 136 includes a plurality of openings. The openings in the retaining mesh 136 are sized to balance airflow through the retaining mesh 136 and the size of the filter media 135. The retaining mesh 136 may alternately be referred to as a filter media mesh and an air permeable sheet. The retaining mesh 136 can be formed from a fine metal mesh, or from other suitable mesh material, such as nylon.

The air treatment panels 130 can removably couple to the basket frame 104. In the depicted embodiment, each of the air treatment panels 130 can be selectively retained in one of the air treatment panel seats 129. Each air treatment panel 130 can include a pair of alignment members 194 along the top edge of the panel frame 132 and a coupler 138 toward the bottom of the panel frame 132. The coupler 138 can be a snap fit coupler that forms a snap fit joint with a complimentary coupler on the basket frame 104. In the current embodiment, the snap fit coupler 138 includes a bias arm 137 with a protrusion 196 and a pressing portion 139.

The air treatment basket 150 can be replenished with new filter media 135. This may be done by replacing installed air treatment panels 130 with new air treatment panels that have fresh filter media or temporarily removing an air treatment panel, replacing the filter media within the panel, and replacing the panel.

Figure 5:
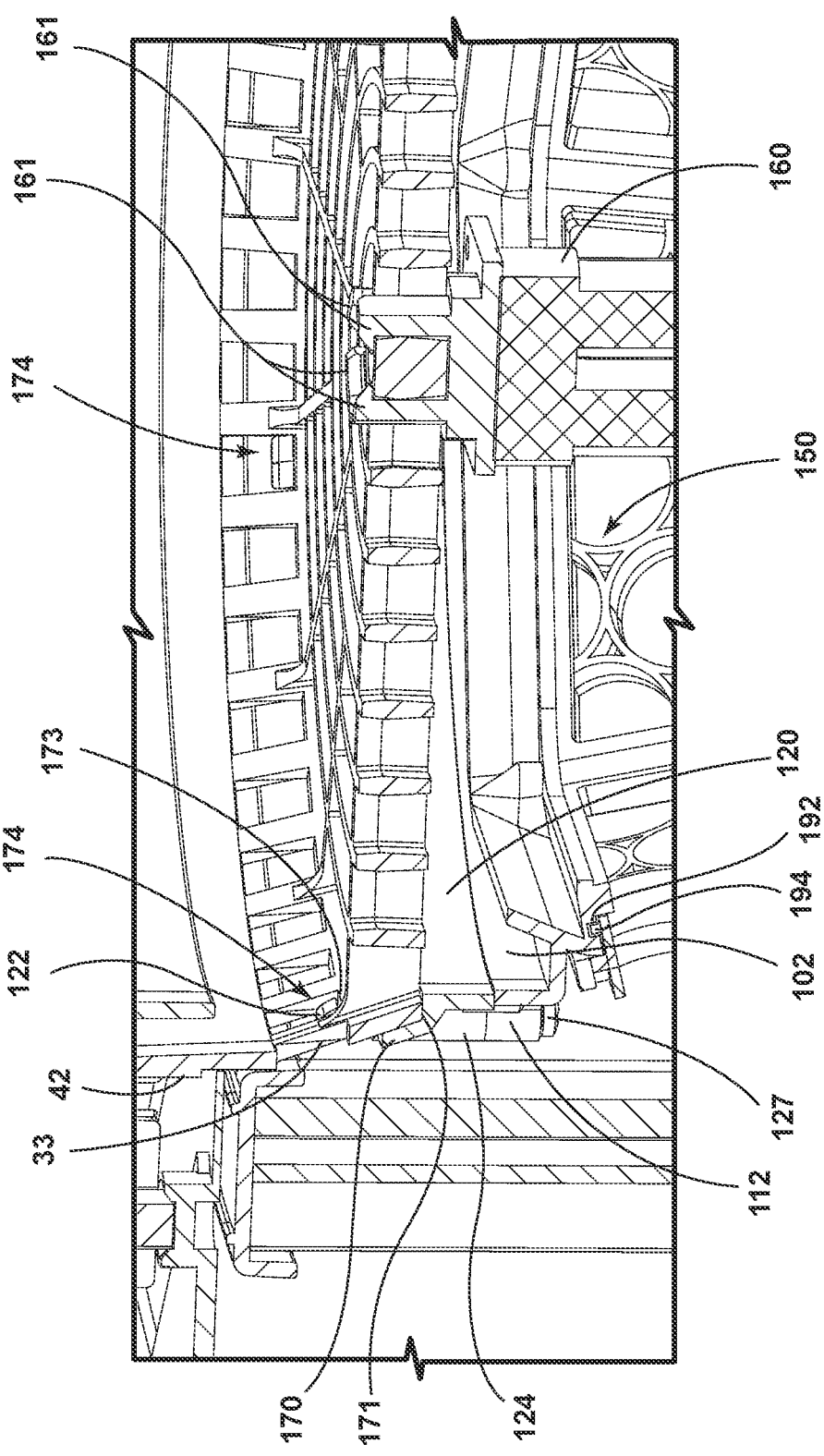
FIG. 5 is a close-up sectional perspective view of the air treatment basket and germicidal light source connection to the airflow grill.

In general, to begin installation of an air treatment panel 130 into the basket frame 104, the pair of alignment members 194 are aligned and slid into the basket frame 104 retention slots 192 (perhaps best shown in FIG. 5).

Figure 9:
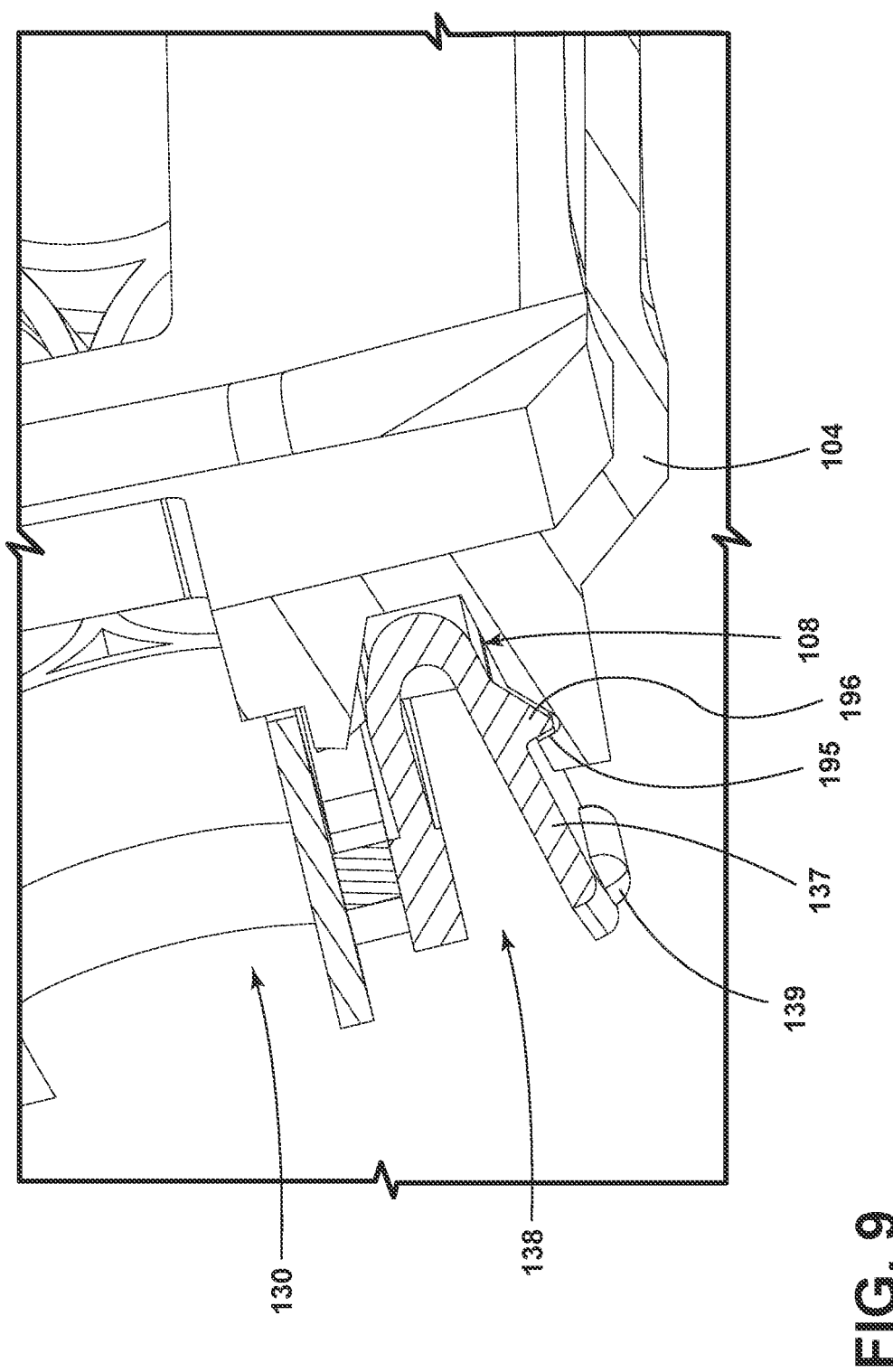
FIG. 9 is a close-up sectional view of a snap fit joint between an air treatment panel and air treatment basket.

FIG. 9 illustrates a close up sectional view of an engaged snap fit joint between an air treatment panel 130 and air treatment basket frame 104. Installation of an air treatment panel 130 into the air treatment basket 150 continues with the pressing portion 139 at the bottom of the panel 130 being depressed to cause the bias arm 137 to deflect for insertion of the snap fit coupler 138 into the channel 108 on the basket frame 104 with the panel coupler 138 protrusion 196 being unimpeded by the channel 108 on the basket frame 104. The pressing portion 139 can then be released such that the bias arm 137 expands to contact a wall of the channel 108 with the protrusion 196 of the panel-side coupler 138 interfitting with and being secured by the basket-side catch 195 of the basket frame 104.

Pressure may be applied to the pressing portion 139 to release the protrusion 196 of the snap fit coupler 138 from the catch 195 of the channel 108 and allow the air treatment panel 130 to be removed from the basket 150. The removable coupling between the coupler 138 and the channel 108 allows the air treatment panels 130 to be individually and selectively removed from the air treatment basket 150 as desired, for example when the filter media 135 is fully saturated or otherwise near end of life. By virtue of having discrete air treatment panels that are individually replaceable, the air treatment basket 150 provides modularity and simplifies filter replacement. The modularity of the air treatment panels 130 improves a user's ability to replace an interior filter (the air treatment basket 150).

The air treatment panels 130 can have a uniform size and shape such that they are interchangeably and selectively mountable to any of the air treatment basket seats 129. In this way, the installation and removal processes for the air treatment panels 130 can be simplified because any of the air treatment panels 130 (or replacement air treatment panels) can mount into any of the seats 129 of the basket frame 104.

General operation of the air purifier and the benefits of a supplemental air treatment device, such as air treatment basket 150, will now be described in detail with respect to an airflow path through the air purifier 10. During operation, the blower 131 draws air through the air purifier 10. The airflow path through the housing 12 includes the air inlet 27 and the air outlet 30. In one embodiment, the airflow path is generally vertical through the housing 12. The air treatment device 38 and air treatment basket 150 are disposed within the airflow path to filter, clean, and/or purify air flowing along the airflow path.

As depicted in FIG. 4, the air treatment basket 150 is in the general shape of a conical frustum. That is, the air treatment basket 150 tapers from a larger diameter toward the top rim 102 to a smaller diameter toward the base 106. The conical shape reduces airflow restrictions across the filter media 135 compared to a traditional cylindrical shape. The air treatment panels 130 are trapezoidal and are seated at a non-vertical angle in the basket frame 104 to make the air treatment basket conform to the conical frustum shape. Put another way, the air treatment panels 130 are installed in the basket frame 104 such that the bottom of the air treatment panel 130 tilts and extends downwardly and inwardly toward the center of the air treatment chamber 25 relative to the top of the panel 130. In the current embodiment, the opening angle, i.e., the angle between the cone center axis and the air treatment panels 130 is about 15 degrees. In alternative embodiments, the angle can be smaller or larger. In some embodiments, the opening angle varies depending on a variety of different factors, such as the height of the air treatment basket, the size and location of the air inlet with respect to the air treatment basket positioning, the size of the air treatment chamber 25, the positioning and length of the germicidal light source (if included), to name a few possible factors. The opening angle can influence the airflow through air treatment panels 130 by changing the airflow relationship between the air flowing from the air inlet 27 to the air treatment panels 130. The relative position and conical shape of the air treatment basket 150 facilitates more uniform airflow to the surface area of each air treatment panel 130 and reduces airflow restrictions or blockage by the basket 150 within the air treatment chamber 25.

The angle of the air treatment panels 130 can affect the way the filter media 135 fills the cells 140. For example, when the air treatment panel 130 is vertical, the filter media 135 will gather at the bottom of the cells 140. When the air treatment panel 130 is disposed at an angle between vertical and horizontal, the filter media 135 will primarily gather at the bottom of the cells 140, but will spread toward the top outer surface of the cells 140 (against the retaining mesh) as the opening angle of the air treatment panel 130 increases toward horizontal.

The germicidal light source 160, if included, can be configured to treat the air in the airflow path as the air passes the germicidal light source 160. The germicidal light source 160 can create a photocatalytic oxidation (PCO) reaction with the filter media 135 in the air treatment basket 150 to help purify the air. For example, the UV-C light can react with a catalyst in the filter media 135 to convert malignant contaminants into water, carbon dioxide, and detritus. The detritus builds up in the filter media 135 and when the filter media 135 is saturated the air treatment panel 130 can be replaced. The conical shape of the air treatment basket 150 including the angle of the air treatment panels 130 relative to the germicidal light source 160 along with the length and positioning of the germicidal light source relative to the panels 130 facilitates a generally uniform amount of UV light reaching the filter media 135 in the cells 140 of the panels 130. Not only does the conical shape of the basket 150 facilitate uninhibited airflow through the purifier as discussed above, but it also facilitates uniform PCO reactions. Because the germicidal light source 160 does not extend all the way to the base 106 of the basket 150, without the conical incline of the air treatment panels 130, the filter media 135 in the cells 140 toward the bottom of the basket would not receive the same amount of UV light, which can cause disproportionate PCO reactions and undesired or inconsistent treatment results.

In the current embodiment, the air treatment basket 150 is mounted to the airflow grill 33. Perhaps as best shown in the close-up sectional perspective view of FIG. 5, the snap fit cantilevers 122 allow the air treatment basket 150 to snap fit to the airflow grill 33 of the lower fan shroud 42. As depicted, the snap fit cantilevers 122 extend vertically from the ring protrusions 124 of the coupling ring 120. The radius of curvature, diameter, and incline of the inclined lip 170 of the coupling ring 120 form a grill seat 171 having a profile that compliments the bottom and outer surfaces of the airflow grill 33. The grill seat 171 provided by the coupling ring 120 facilitates alignment of the air treatment basket 150 such that the snap fit cantilevers 122 bend and snap fit onto the horizontal catch surface 173 of select slits 174 on the inclined edge of the airflow grill. In alternative embodiments, the snap fit cantilevers 122 and horizontal catch surfaces 173 may be any suitable coupling assembly that can fix the air treatment basket 150 within the air treatment chamber 25. Perhaps as best shown in FIG. 8, a plurality of slits 174 can be uniformly spaced around a perimeter of the grill 33 such that the air treatment basket 150 can be mounted to the airflow grill 33 in a variety of orientations. Put another way, the snap fit cantilevers 122 can bend and snap fit onto the horizontal catch surface 173 of any of the slits 174 depending on the rotational orientation of the air treatment basket 150.

While the depicted embodiment contemplates that the air treatment basket 150 is installed permanently within the air treatment chamber with modular panels 130 being selectively removable without removing the air treatment basket 150, in alternative embodiments, the air treatment basket 150 as a whole can be removable from the air treatment chamber 25. For example, an inclined surface (not shown) can be provided at the top of the slits 174 of the airflow grill 33 such that application of vertical upward force on the basket 150 will cause the snap fit cantilevers 122 to press against the inclined surface and deflect outward and disconnect the snap fit joint. In another embodiment, the air treatment basket 150 may be removed from the air purifier 10 by a user grasping the air treatment basket 150 and twisting it from a locked position to an unlocked position. The grill 33 can include a receiving portion that may taper from a wider width to a smaller width. In the locked position, the attachment mechanism 122 may be friction fit into the receiving portion at the smaller width. In the unlocked position, the attachment mechanism 122 is in the wider width of the receiving portion. Once in the unlocked position, the air treatment basket 150 may be removed from the air purifier 10. To install the accessory 150, the user can insert the air treatment basket 150 in the unlocked position and twist it to the locked position. Other installation, removal, and securing methods are possible.

Figure 6:
FIG. 6 is a sectional perspective view of the base of an air treatment basket according to one embodiment.
Figure 6:
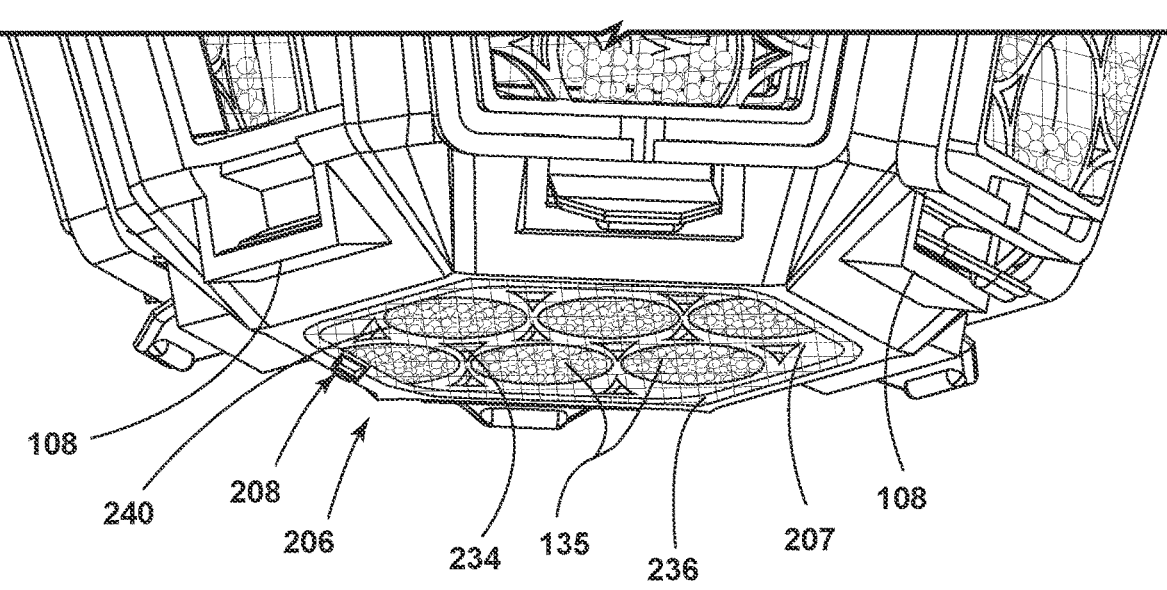

FIG. 6 depicts a sectional perspective view of an alternative embodiment having an air-permeable base 206 that permits airflow into the basket 150. The air-permeable base 206 can include a base frame 207 and base filter media matrix 207. The base frame can have a matrix that can include a plurality of cells 240 filled with filter media 135 retained within the cells 240 by retaining mesh 236, similar to the air treatment panel matrix 131. The base filter media matrix 207 has a horizontal orientation such that the filter media 135 generally spreads across the bottom surface of the cell 240 rather than collecting toward one end of the cell due to gravity like in the inclined air treatment panels 130. The amount of filter media in the base cells 240 may be adjusted such that sufficient airflow can be permitted through the cells of the air-permeable base 206 and such that suitable PCO reactions are facilitated by the UV light from the germicidal light source, if included. For example, the filter media 135 can be spread across the cell thinly enough to facilitate sufficient airflow and PCO reactions. Open spaces 234 can be provided between the cells 240 to facilitate airflow through the base 206. The air treatment basket frame 104 can define a channel 208 for securing the base 206 to the basket frame 104 in a similar fashion to the air treatment panels 130 securing to the basket frame 104 through the channel 108. The base 206 may alternately be secured to the basket frame 104 through any suitable fastener.

Figure 7:
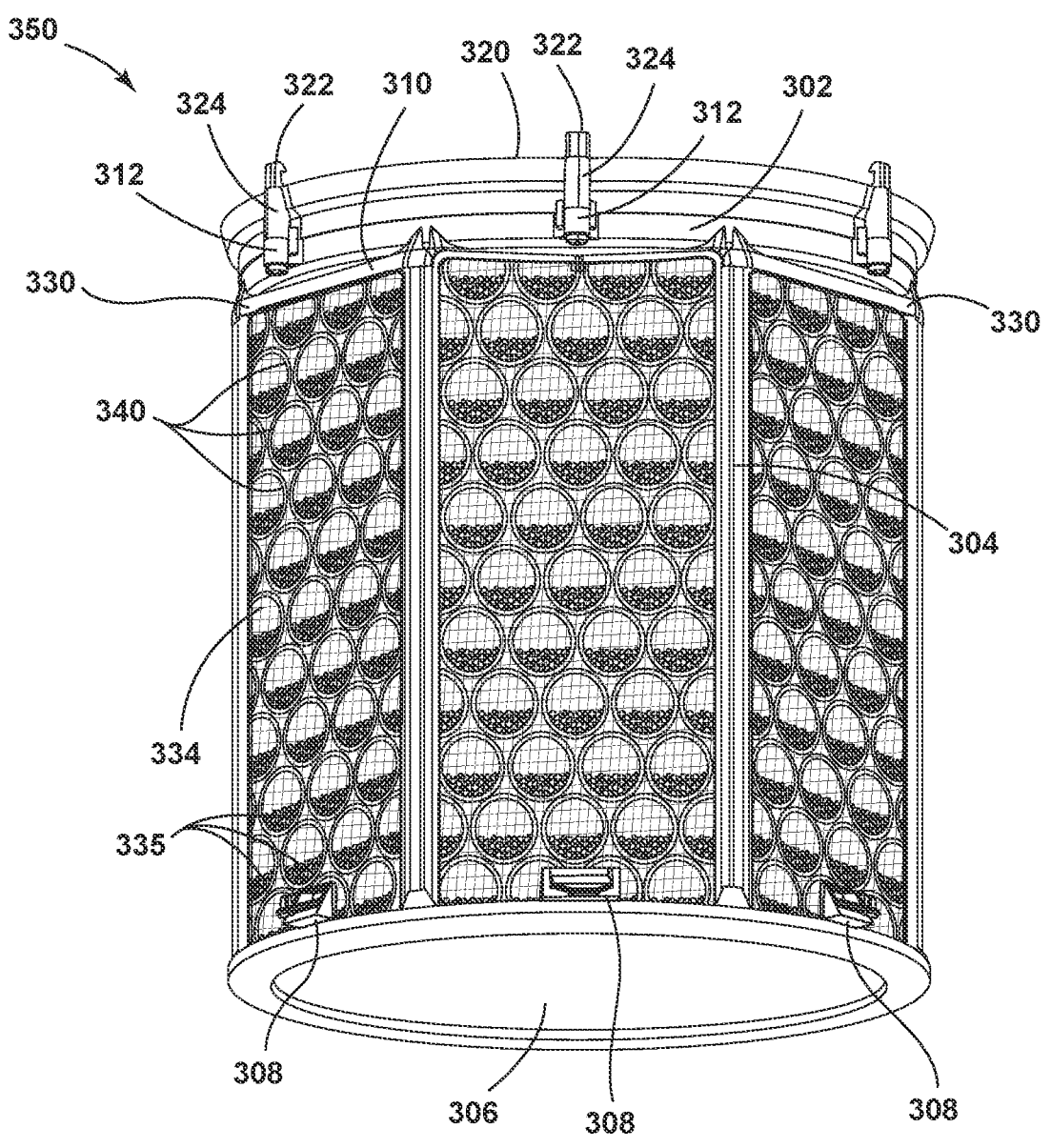
FIG. 7 is a perspective view of an air treatment basket according to one embodiment.

FIG. 7 depicts an air treatment basket 350 according to another aspect of the disclosure. The air treatment basket 350 of FIG. 7 has many of the same features as the air treatment basket discussed with respect to the preceding figures except for the differences outlined below. The air treatment basket 350 of FIG. 7 has a shape that is complementary to the interior of the air treatment device or interior of the air treatment chamber walls. The air treatment panels 330 have a rectangular shape and are secured to the air treatment basket frame 304 in a vertical position. As such, the filter media 335 may fill the cells 340 differently than in the conical air treatment basket. In an alternate embodiment, the air treatment panels 330 can be generally rectangular in shape but be curved to match the contour of the base 306.

The terms "comprising" or "comprise" are used herein in their broadest sense to mean and encompass the notions of "including," "include," "consist(ing) essentially of," and "consist(ing) of." The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples.

The above description relates to general and specific embodiments of the disclosure. However, various alterations and changes can be made without departing from the spirit and broader aspects of the disclosure as defined in the appended claims, which are to be interpreted in accordance with the principles of patent law including the doctrine of equivalents. As such, this disclosure is presented for illustrative purposes and should not be interpreted as an exhaustive description of all embodiments of the disclosure or to limit the scope of the claims to the specific elements illustrated or described in connection with these embodiments. Any reference to elements in the singular, for example, using the articles "a," "an," "the," or "said," is not to be construed as limiting the element to the singular.

What is claimed is:

1. An air purifier comprising:
  a housing including an air inlet, an air treatment chamber, and an air outlet;

an airflow path fluidly connecting the air inlet, the air treatment chamber, and the air outlet;

a blower disposed within the housing, the blower configured to draw air into the housing through the air inlet, along the airflow path, and push air out of the housing through the air outlet; and an air treatment basket supported by the housing and disposed within the air treatment chamber, wherein the air treatment basket is configured to at least one of filter, clean, and purify air flowing through the airflow path, the air treatment basket including:

an air treatment basket frame defining a plurality of air treatment panel seats; and a plurality of air treatment panels configured to removably couple to the air treatment basket frame, the plurality of air treatment panels each including a filter media, wherein the plurality of air treatment panels are disposed in the airflow path;

wherein the plurality of air treatment panels are individually and selectively removeable from the air treatment basket frame.

2. The air purifier of claim 1, further comprising:

a germicidal light source supported by the housing, the germicidal light source disposed at least partially within the air treatment basket frame, wherein the germicidal light source is configured to treat air in a portion of the air flow path.

3. The air purifier of claim 2, wherein the germicidal light source is an ultraviolet light.

4. The air purifier of claim 3, wherein the germicidal light source is configured to generate a photocatalytic oxidation in the filter media of the plurality of air treatment panels.

5. The air purifier of claim 1, further comprising a supplementary air treatment device disposed in the air treatment chamber, the supplemental air treatment device configured to at least partially surround the air treatment basket.

6. The air purifier of claim 5, wherein the supplemental air treatment device is a 3-in-1 filter including a pre-filter and combination of carbon and HEPA filter.

7. The air purifier of claim 1, wherein the plurality of air treatment panels are nonparallel to the housing.

8. The air purifier of claim 1, wherein each of the plurality of air treatment panels includes a filter media matrix having a plurality of cells at least partially filled with the filter media.

9. The air purifier of claim 8, wherein each of the plurality of air treatment panels includes a retaining mesh configured to retain the filter media in the plurality of cells of the filter media matrix.

10. The air purifier of claim 9, wherein the filter media is at least one of a granulate, particulate, and pelletized filter media or any combination thereof.

11. The air purifier of claim 10 wherein a filter media fill percentage for the plurality of air treatment panels is selected to provide a suitable filter media distribution and airflow profile through the filter media matrix.

12. The air purifier of claim 1, the air treatment basket frame having a conical frustum shape with an airflow non-permeable base.

13. An air treatment basket for use with an air purifier, the air treatment basket comprising:

an air treatment basket frame defining an exit aperture, a plurality of air treatment panel seats, and a base; and a plurality of air treatment panels configured to be seated and retained in the air treatment panel seats, the plurality of air treatment panels each including a filter media matrix having a plurality of cells containing filter media;

wherein while the plurality of air treatment panels are seated in the air treatment panel seats and the air treatment basket is operably installed within an air treatment system, the air treatment panels are inclined such that the filter media contained within the plurality of cells of the filter media matrix of the plurality of air treatment panels gathers toward the bottom of the cells permitting airflow adjacent the filter media in the plurality of cells; and wherein each of the plurality of air treatment panels are individually and selectively removeable from the air treatment basket frame.

14. The air treatment basket of claim 13, wherein the air treatment basket frame is shaped as a conical frustum.

15. The air treatment basket of claim 13, wherein the air treatment basket frame is shaped as a cylinder.

16. The air treatment basket of claim 13, wherein the base has a smaller diameter than the exit aperture.

17. The air treatment basket of claim 13, each of the plurality of air treatment panels further including a retaining mesh configured to retain the filter media in the plurality of cells.

18. The air treatment basket of claim 17, wherein the filter media is at least one of a granulate, particulate, and pelletized filter media or any combination thereof.

19. The air treatment basket of claim 13, the base including a base frame removably couplable to the air treatment basket frame, the base frame including a base filter media matrix, wherein the base frame permits airflow into the air treatment basket.

20. The air purifier of claim 1, wherein the plurality of air treatment panels are individually and selectively removeable from the air treatment basket frame while the air treatment basket frame remains within the air treatment chamber.

* * * * *